United States Patent
Lloyd et al.

(10) Patent No.: US 6,186,962 B1
(45) Date of Patent: *Feb. 13, 2001

(54) METHOD AND DEVICE FOR DETECTING EDEMA

(75) Inventors: Lester John Lloyd, Orinda; Jorah Wyer, Mountain View, both of CA (US)

(73) Assignee: Alere Incorporated, San Francisco, CA (US)

(*) Notice: Under 35 U.S.C. 154(b), the term of this patent shall be extended for 0 days.

This patent is subject to a terminal disclaimer.

(21) Appl. No.: 09/327,153

(22) Filed: Jun. 7, 1999

Related U.S. Application Data

(62) Division of application No. 08/959,001, filed on Oct. 28, 1997.

(51) Int. Cl.[7] .............................. A61B 5/00; A61B 5/103
(52) U.S. Cl. .................... 600/587; 600/300; 128/903; 128/904; 340/573.1
(58) Field of Search .................... 600/561, 587, 600/592, 595, 300, 301, 481; 73/81; 340/500, 540, 573.1

(56) References Cited

U.S. PATENT DOCUMENTS

| | | | |
|---|---|---|---|
| 3,791,375 | 2/1974 | Pfeiffer | 128/2 S |
| 3,850,034 | * 11/1974 | Tsuchiya et al. | 600/592 |
| 3,890,958 | 6/1975 | Fister et al. | 128/2 S |
| 3,974,491 | 8/1976 | Sipe | 340/272 |
| 4,132,224 | * 1/1979 | Randolph | 128/2 S |
| 4,144,749 | 3/1979 | Whitmore | 73/149 |
| 4,159,640 | * 7/1979 | Leveque et al. | 600/587 |
| 4,383,533 | 5/1983 | Bhagat et al. | 128/660 |
| 4,611,487 | * 9/1986 | Krenn et al. | 73/81 |
| 4,838,275 | 6/1989 | Lee | 128/670 |
| 4,951,671 | * 8/1990 | Coan | 600/587 |

(List continued on next page.)

OTHER PUBLICATIONS

Boland, R. et al., "Development and Evaluation of a Precision Forearm and Hand Volumeter and Measuring Cylinder," *J. Hand Ther* (1996), vol. 9, No. 4:349–358.

Breytenbach, H.S., "Objective Measurement of Post–Operative Swelling," *Int. J. Oral Surg.* (1978) vol. 7:386–392.

Dramaix, M. et al., "Serum Albumin Concentration, Arm Circumference, and Oedema and Subsequent Risk Of Dying In Children In Central Africa," *BMJ* (1993) vol. 307:710–713.

Kushner, Robert F., et al., "Estimation of Total Body water By Bioelectrical Impedance Analysis[1–3]," *The American journal of Clinical Nutrition* (1986) vol. 44:417–424.

Lindahl, O.A., et al., "Impression Technique for the Assessment of Oedema: Comparison With A New Tactile Sensor That Measures Physical Properties Of Tissue," *Med. & Biol. Eng. & Comput.*, (1995) vol. 33:27–32.

(List continued on next page.)

*Primary Examiner*—Cary O'Connor
*Assistant Examiner*—Charles Marmor, II
(74) *Attorney, Agent, or Firm*—Karl Bozicevic; Bozicevic, Field & Francis LLP

(57) ABSTRACT

Methods and devices are provided for detecting the presence of edema in a mammalian host. In the subject methods, a device comprising a planar surface and a probe extendable therefrom is contacted with the surface of the extremity. The probe is then extended from the planar surface in a manner sufficient to form a depression or "pit" in the skin surface of the extremity. The probe is then held in constant position relative to the planar surface and the extremity for a period of time during which a plurality of force measurements and a force profile is generated therefrom. The force profile is then related to the presence of edema in the patient. The subject methods find use in the diagnosis and management of diseases characterized by the presence of edema as a physical manifestation, particularly congestive heart failure.

7 Claims, 1 Drawing Sheet

Probe Pressed Into Skin

U.S. PATENT DOCUMENTS

| | | | | |
|---|---|---|---|---|
| 5,027,828 | * | 7/1991 | Kovacevic et al. | 128/774 |
| 5,052,405 | | 10/1991 | Batchelder | 128/774 |
| 5,323,650 | | 6/1994 | Fullen et al. | 73/172 |
| 5,373,730 | * | 12/1994 | Kovacevic | 600/587 |
| 5,385,069 | | 1/1995 | Johnson, Jr. | 73/571 |
| 5,433,215 | * | 7/1995 | Athanasiou et al. | 600/587 |
| 5,551,437 | * | 9/1996 | Lotscher | 128/672 |
| 5,590,649 | * | 1/1997 | Caro et al. | 128/630 |
| 5,671,750 | * | 9/1997 | Shinoda | 128/672 |

OTHER PUBLICATIONS

Miyazaki, S., et al., "Foot–Force Measuring Device For Clinical Assessment of Pathological Gait," *Med. & Biol. Eng. & Comput.* (1978) vol. 16:429–436.

Mridha, M. et al., "Fluid Translocation Measurement," *Scand j Rehab Med* (1989) vol. 21:63–69.

Mridha, M., et al., "Noninvasive Method For The Assessment of Subcutaneous Oedema," *Medical & Biological Engineering & Computing* (1986) vol. 24:393–398.

_., "An Automatic Device For The Measurement of Oedema In The Feet Of Rats and Guinea Pigs," *Med. & Biol. Enging.* (1971) vol. 9:567–570.

Starr, Thomas W., "A Computerized Device for the Volumetric Analysis of the Residual Limbs of Amputess," *Bulletin of Prosthetics Research BPR 10–33* (1980) vol. 17, No. 1,:98–102.

Swedborg, Iwona, "Voluminmetric Estimation of the Degree of Lymphedema and its Therapy By Pneumatic Compression," *Scand J Rehab Med* (1977) vol. 9:131–135.

* cited by examiner

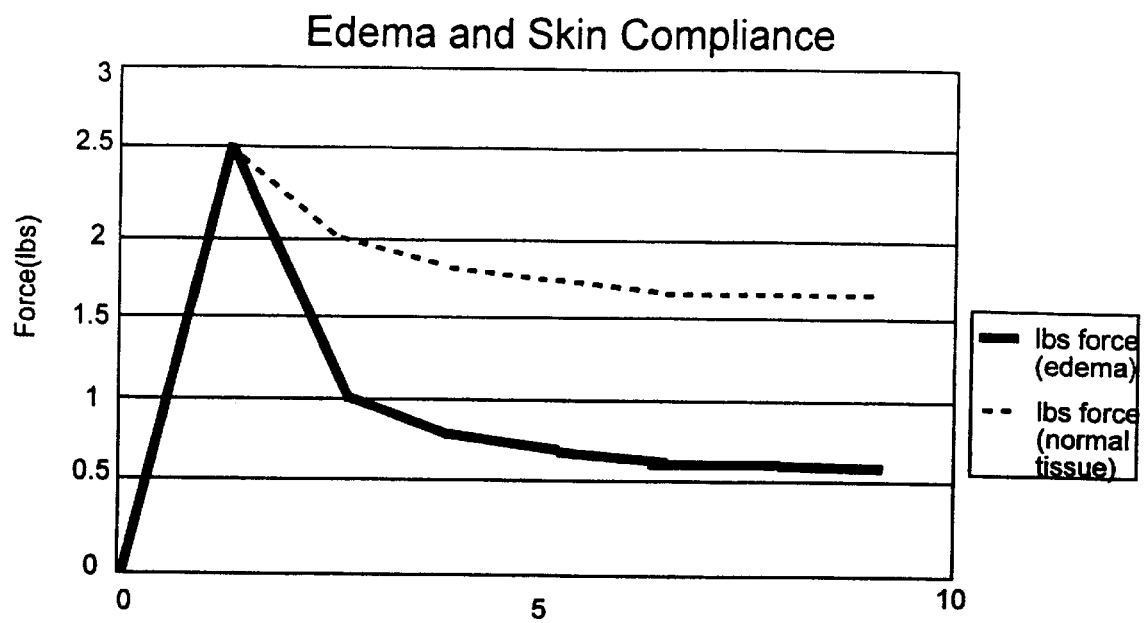
FIG. 1
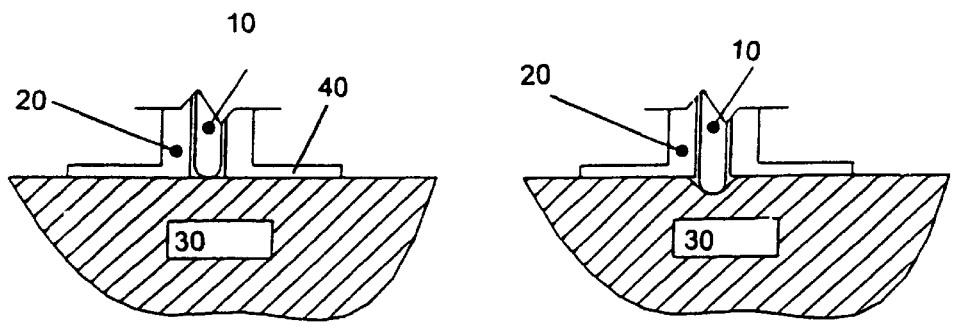
Probe Flush With Plate
FIG. 2A
Probe Pressed Into Skin
FIG. 2B

METHOD AND DEVICE FOR DETECTING EDEMA

CROSS-REFERENCE TO RELATED APPLICATION

This application is a division of application Ser. No. 08/959,001, filed on Oct. 28, 1997; the disclosure of which is herein incorporated by reference.

INTRODUCTION

1. Technical Field

The field of this invention is diseases characterized by edema.

2. Background of the Invention

Edema is defined as the abnormal accumulation of fluid in connective tissue. Edema typically results from a combination of passive venous congestion and salt and water retention, and may be systemic or localized to a particular region of the body. Dependent edema, in which fluid accumulates in the tissues of the limbic extremities, e.g. ankle, foot and the like, is a physical manifestation of a number of different human disease conditions. Dependent edema first appears in the feet and ankles of the ambulatory patient, and in the posterior surface of the calves and skin overlying the sacrum in the bedridden patient. Disease conditions characterized by the presence of dependent edema include local venous or lymphatic obstruction, cirrhosis, hypoalbumenia, and congestive heart failure.

In congestive heart failure, the presence of edema in the lower extremities is a valuable diagnostic marker for the presence of the disease. In addition to serving as a marker for the presence of congestive heart failure, the progression of the edemic state can be monitored over time and the progression of the edemic state related to the progression of the disease.

One way of detecting the presence of edema is to determine fluid volume change of the patient. A number of different technologies have been developed to identify the volume change, and include those based on the use of water or air-filled cuffs, mercury strain gauge, fiber optic strain gauge, and airborne ultrasound. Such technologies have principally been employed to measure venous blood flow and to sense the volume pulsations created by the heart.

Another way of detecting the presence of edema is the "pitting" method. In this method, a physician's thumb or finger is pressed into the patient's skin next to a bony surface (e.g., tibia, fibula, or sacrum). When the physician's finger is withdrawn, an indentation persists for a short time. The depth of the "pit" is estimated and generally recorded in millimeters, although subjective grading systems (e.g. "+++", etc.) have also been described. In general, the distribution of edema is also noted, as the amount of fluid is roughly proportional to the extent and the thickness of the pit.

Because dependent edema is a physical manifestation of a number of different disease conditions, the development of accurate methods for the detection of edema is of interest. Of particular interest is the development of methods which are sufficiently inexpensive and simple so as to be amenable to use in both conventional and out-patient health-care settings.

Relevant Literature

Scientific American Medicine (Dale & Freeman eds)1:II provides a review of congestive heart failure, physical manifestations and methods for the treatment thereof.

Lindahl & Omata, Med. Biol. Eng. Comput. (1995) 33:27–32 provide a description of methods of assessing edema.

Other references of note include U.S. Pat. Nos. 3,791,375; 3,890,958; 3,974,491; 4,144,749; 4,383,533; 5,052,405; 5,323,650; and 5, 385,069; as well as Swedborg, Scand. J. Rehab. Med. (1977) 9:131–135; Mridha & Odman, Scand. J. Rehab. Med. (1989)21:63–39; Mridha & Odman, Med. Biol. Eng. Comput. (1986) 24: 393–398; Kushner et al., Am. J. Clin. Nut. (1986) 44: 417–424; Breytenbach, Int. J. Oral Surg. Bozicevic & Reed Ref: ALE-4P (1978) 7:386–392; Davies et al., Med. Biol. Eng. Comput. (1971) 9:567–570; Lindhal et al., Med. Biol. Eng. Comput. (1991) 29: 591–597; Iwakura, Med. Biol. Eng. Comput. (1978) 16:429–436; and Starr, BPR (1980) 17:98–102.

SUMMARY OF THE INVENTION

Methods and devices for measuring the presence of and/or monitoring the progression of edema in a host are provided. In the subject methods, an extremity of a host is first contacted with a force sensor means comprising a planar surface and a probe element extendable therefrom. The probe element is then extended from the planar surface into the tissue of the extremity to produce a depression or pit. A plurality of force measurements are then taken over a period of time to obtain a force profile. The resultant force profile is then related to the presence or absence of edema in the patient. The subject methods find use in a variety of applications, particularly in the detection and management of cardiac associated diseases where edema serves as a symptom.

BRIEF DESCRIPTION OF THE FIGURES

FIG. 1 shows a representative force profile obtained according to the subject invention.

FIGS. 2a and 2b show a force sensor means and its use according to the subject invention.

DESCRIPTION OF THE SPECIFIC EMBODIMENTS

Methods and devices for measuring the presence of and/or monitoring the progression of edema in a host are provided. In the subject methods, an extremity of a host is first contacted with a force sensor means comprising a planar surface and a probe element extendable therefrom. The probe element is then extended from the planar surface into the tissue of the extremity to produce a depression or pit. A plurality of force measurements are then taken over a period of time to obtain a force profile. The resultant force profile is then related to the presence or absence of edema in the patient. The subject find use in the diagnosis and management of diseases characterized by the presence of edema, particularly congestive heart failure.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

In describing the subject invention, first the device employed in the subject methods will be described in greater detail followed by a more detailed description of the methods of using the device to detect edema in a host. The device comprises a planar surface having a force probe extendable therefrom. The planar surface will generally be a plate or other similar structure, where the plate like structure may be configured in a variety of different shapes, such as a square, rectangle, circle, oval or other suitable shape. Plate like structures are suitable for use in situations where one desires to contact only a partial region of the extremity. Alternatively, the planar surface may be the inner surface of a cuff or other similar structure which surrounds the extremity in the region of interest. The planar surface may be the surface of a number of distinct materials, including metals, such as aluminum, stainless steel and the like, or more pliant materials, such as polymeric materials, e.g. synthetic foam materials, Delrin, polyethylene, teflon, naturally occurring materials, e.g. rubber, wood, and the like.

In addition to the planar surface, the devices of the subject invention comprise a probe extendable from the planar surface of the device. Conveniently, the planar surface will comprise an orifice or opening, usually in a central region of the planar surface, from which the probe is extendable. The probe comprises a force sensor, where any convenient force sensor capable of collecting force data and relating it to a processing means (in those embodiments comprising a processing means) may be employed. Suitable types of force sensors which the probe may comprise include: loadcells (as described in U.S. Pat. No. 5,370,535, the disclosure of which is herein incorporated by reference), spring activated adjustable force sensors with microswitches, and the like.

A representative device according to the subject invention is shown in FIGS. 2a and 2b. The device comprises a planar surface 40 of a plate component 20 and a probe 10 which extends from the planar surface towards the skin 30 during use, as explained in greater detail below.

In addition to the above components, the device may further comprise a number of additional components which assist in the measurement and/or generation of the force profile, as described below. One such element is a second plate or similar structure which is opposite the planar surface that serves a reference for the probe, e.g. in a C-clamp fashion. The device may also comprise a processing means for generating a force profile from the gathered measurements. Other elements that may be included in the device are: motors, such as a stepper motor, etc.

Turning now to the subject methods, the first step of the subject methods is to contact a region of the extremity with the planar surface. The amount of pressure applied upon contact should be sufficient to keep the planar surface in a constant location in relation to the limb, yet not so great as to depress the planar surface below the surface of the extremity. Suitable contact can be achieved a number of different ways, depending on the particular device configuration being employed. For example, the host may simply press the extremity lightly against the planar surface. Alternatively, the device comprising the planar surface may have a second plate positioned opposite the planar surface, between which the extremity is placed and which may be tightened in a C-clamp fashion to provide for the requisite contact. In yet another embodiment where the device is in the form of a cuff that surrounds or encircles the extremity at the region of interest, the cuff may be tightened a sufficient amount to provide for a tight fit and the requisite contact.

After sufficient contact between the planar surface and the extremity is achieved, the probe comprising the force sensor is then extended from the planar surface against the extremity surface resulting in the production of a "pit" in the surface of the extremity. The force employed to extend the probe will be sufficient to generate the depression or pit and will generally range from about 0.1 to 4.0 cm, usually from about 0.3 to 3.0 cm and more usually from about 0.2 to 2.0 cm. The rate at which the probe is extended will vary between about 0.25 and 4.0 cm/sec, usually from about 0.5 to 2 cm/sec. The probe will continue to be pressed against the surface of the skin of the extremity until a predetermined force is reached, where that force will generally range from about 0.1 to 5.0 kg, usually from about 0.2 to 3.0 kg and more usually from about 0.5 to 2.0 kg. Once the predetermined and specified force is reached, the probe is maintained for a period of time at a constant position relative to the extremity and the planar surface of the device, during which time a plurality of force measurements are recorded. The period of time that contact is maintained will be sufficient to perform the desired number of force measurements, where generally the period of time will range from about 1 to 20 seconds, usually from about 2 to 10 seconds and more usually from about 3 to 5 seconds. The number of force measurements taken during the period of time will be sufficient to obtain a suitable number of data points to generate a sufficiently detailed force profile, as described in greater detail below, and will be at least 1, usually at least 2 and more usually at least 5 and may be great as 20 or greater, but will usually not exceed 10 in number.

The above steps result in the generation of a series of force measurements over time. This force measurement data is then forwarded (e.g. transferred, transmitted, etc.) to a processing means which generates or derives a force profile, as shown in FIG. 1, from the obtained series of force measurements. The processing means may be a human who manually plots the data points to generate the force profile, e.g. a nurse or physician, or a means that automatically generates the profile from the data, such as a microprocessor means. The processing means to which the data is forwarded from the sensor and which derives the force profile from the data may be part of the device or part of a monitoring system that is operationally linked to the subject device, where a representative monitoring system includes the patient interface system described in U.S. patent application Ser. No. 08/958,689 filed Oct. 28, 1997 issued Jun. 27, 2000 as U.S. Pat. No. 6,080,106 entitled Patient Interface System and filed concurrently herewith, the disclosure of which is herein incorporated by reference.

The resultant measured force profile is then compared to a control profile. The control profile will be a profile which corresponds to that which would be generated in the absence of the edemic state. Where possible to measure the limb in the absence of edema, such as in the case of pregnancy or prior to surgery that causes edema, when the measurement can be made at an early time in anticipation of later indications of edema, then such non-edemic measurements can be used as a control profile. Most often this is not possible as the desirability of edemic measurements is not apparent until the edema is already a problem. In this case the best indication of the non-edemic control profile is simply the lowest value obtained from a series of profiles taken over a period of time. If a microprocessor or other computer device is available, then the recording and displaying of the measurements allows an instant graphic display of not only the measured amount of edema but, often more importantly, whether the condition is worsening or improving. The measured profile and the control profile will be compared and any difference will be identified.

The presence of a difference between the measured and control profiles is then correlated to the presence of swelling in the region of measurement and edema in the patient. Conversely, the absence of a difference may be related to the absence of the edemic state. Accordingly, the final step of the subject methods is to attribute the presence of a difference to the presence of edema in the patient.

The subject methods may be used to make multiple profiles over a given period of time so that the progression of the edemic state may be monitored. Where multiple profiles are the measurements will typically be made according to a schedule, where the measurements may be made hourly, daily, weekly, monthly and the like.

A microprocessor may be used in conjunction with the subject methods. For example, the measured profile may be input into a microprocessor device that then takes the data and performs the comparison with a predetermined control value and provides a readout of any difference. The microprocessor could also transmit the input data to a remote site for further processing and use. Such an embodiment finds use in applications were measurements are taken at sites remote to the medical personnel in charge of interpreting the results, such as in outpatient clinics, at the home and the like.

The subject methods find use with a variety of mammalian hosts where the detection of dependent edema is desired. Mammalian hosts with which the subject methods may find use include highly valuable, rare and exotic animals, domestic animals, such as livestock and pets, and humans.

Of particular interest is the use of the subject methods in the diagnosis and management of human diseases in which dependent edema is a physical manifestation, such as venous or lymphatic blockage, cirrhosis, hyperalbumenia and congestive heart failure, where congestive heart failure is of particular interest.

In using the subject methods in the diagnosis of congestive heart failure, the detection of edema by the subject methods is used as an indication of the presence of congestive heart failure. In making such diagnoses, jugular venous distention may be detected, since the presence of both conditions can be used as assurance that the underlying disease condition is congestive heart failure, and not another disease characterized by the presence of dependent edema, such as local venous or lymphatic obstruction, cirrhosis or hypoalbumenia.

Also of particular interest is the use of the subject methods in the management of congestive heart failure. In managing congestive heart failure, a plurality of measurements will be taken according to a schedule and the progression the edemic state will be monitored. In this manner, the affect of various treatment methodologies on the symptoms associated with and/or the progression of the underlying disease can be assessed.

The following examples are offered by way of illustration and not by way of limitation.

EXPERIMENTAL

A sixty one year old man with congestive heart failure resides at home with a care giver. A computerized telephonic monitoring system is installed which transmits information to a centralized nursing station. The system requires the patient to complete a daily monitoring cycle which includes answering questions on his general health, sleeping, appetite, and any unusual symptoms. As well, the device shown in FIGS. 2a and 2b is employed to generate a force profile as depicted in FIG. 1. The patient presses a button to record the measurements and, following generation of the force profile, removes the apparatus. At a later time, the computer system transmits the entire information set collected, including the edema measurements, to the central station. With an analysis of this daily information, a physician has early warning information, and can provide prompt care, avoiding acute episodes. Of particular interest is use of the subject methods and devices as part of the patient interface system disclosed in U.S. patent application Ser. No. 08/958,689 filed Oct. 28, 1997 issued Jun. 27, 2000 as U.S. Pat. No. 6,080,106 entitled Patient Interface System and filed concurrently herewith, the disclosure of which is herein incorporated by reference.

It is evident from the above results and discussion that improved methods for detecting dependent edema in a mammalian host are provided. Because the subject methods use relatively simple and inexpensive measurement devices, they are amenable or use in high volume situations and out patient settings by moderately skilled personnel, and therefore provide an attractive alternative to currently employed methods of detecting edema which are based on the detection of volume changes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A patient interface system for use in collecting and transferring data from a patient to a remote monitoring system, said system comprising:
   (a) a patient data input and data receiving means comprising:
      (i) a device for detecting edema in an extremity of a host; and
      (ii) an interrogation means;
   (b) a processing means capable of receiving and storing data from the patient data input means;
   (c) a communication means capable of transferring processed patient data from the processing means to a remote monitoring system and receiving instructional data from the remote monitoring system.

2. The system of claim 1, wherein the device for detecting edema comprises:
   a planar surface; and
   a probe extendable from the planar surface, wherein the probe comprises a force sensor.

3. The system according to claim 1, wherein said processing means is further capable of storing a predetermined target value and a series of questions.

4. The system according to claim 3, wherein said processing means is further capable of comparing a sensor measured physiological parameter with said predetermined target value to determine a variance.

5. The system according to claim 3, wherein said processing means is capable of accepting and storing a new predetermined target value and series of questions from said remote monitoring system.

6. The system according to claim 1, wherein said interrogation means further comprises at least one of a keyboard, a plurality of buttons and a microphone.

7. The system according to claim 1, wherein said communication means comprises at least one of a modem, a serial interface, a LAN connection and a wireless transmitter.

* * * * *